(12) United States Patent
Sletta et al.

(10) Patent No.: US 10,494,375 B2
(45) Date of Patent: Dec. 3, 2019

(54) ANTIMICROBIAL COMPOUND

(71) Applicant: SINTEF TTO AS, Trondheim (NO)

(72) Inventors: Havard Sletta, Trondheim (NO); Kristin Flogstad Degnes, Trondheim (NO); Trond Erling Ellingsen, Ranheim (NO); Anna Nordborg, Trondheim (NO); Geir Klinkenberg, Heimdal (NO); Sigrid Hakvag, Trondheim (NO)

(73) Assignee: SINTEF TTO AS, Trondheim (NO)

( * ) Notice: Subject to any disclaimer, the term of this patent is extended or adjusted under 35 U.S.C. 154(b) by 0 days.

(21) Appl. No.: 16/095,143

(22) PCT Filed: Apr. 21, 2017

(86) PCT No.: PCT/EP2017/059521
§ 371 (c)(1),
(2) Date: Oct. 19, 2018

(87) PCT Pub. No.: WO2017/182632
PCT Pub. Date: Oct. 26, 2017

(65) Prior Publication Data
US 2019/0135822 A1    May 9, 2019

(30) Foreign Application Priority Data

Apr. 22, 2016 (NO) .................................. 20160680

(51) Int. Cl.
*C07D 491/052* (2006.01)
*A61P 31/04* (2006.01)
*C12P 17/18* (2006.01)

(52) U.S. Cl.
CPC .......... *C07D 491/052* (2013.01); *A61P 31/04* (2018.01); *C12P 17/18* (2013.01)

(58) Field of Classification Search
CPC ....... C07D 491/052; A61P 31/04; C12P 17/18
See application file for complete search history.

(56) References Cited

FOREIGN PATENT DOCUMENTS

| DE | 102006002427 A1 | 7/2007 |
| WO | 2007095696 A1 | 8/2017 |

OTHER PUBLICATIONS

Englehardt et al.; "Production of a New Thiopeptide Antibiotic, TP-1161, by a Marine *Nocardiopsis* Species"; Applied and Environmental Microbiology; 76(15); pp. 4969-4976; (2010).
International Preliminary Report on Patentability; International Application No. PCT/EP2017/059521, International Filing date Apr. 21, 2017; dated Apr. 19, 2018; 13 pages.
International Search Report and Written Opinion; International Application No. PCT/EP2017/059521; International Filing Date Apr. 21, 2017; dated Jul. 21, 2017; 15 pages.
NO 20160680 Search Report dated Oct. 28, 2016; 3 pages.
Terui et al.; "Xantholipin, a Novel Inhibitor of HSP47 Gene Expression Produced by *Streptomyces* sp."; Tetrahedron Letters; 44(29), pp. 5427-5430; (2003).
Winter et al.; "Polycyclic Xanthone Natural Products: Structure, Biological Activity and Chemical Synthesis"; Natural Product Reports; 30(3); p. 382-391; (2013).
Zhang et al.; "Unveiling the Post-PKS Redox Tailoring Steps in Biosynthesis of the Type II Polyketide Antitumor Antibiotic Xantholipin"; Chemistry and Biology; 19(3); pp. 422-432; (2012).

*Primary Examiner* — Timothy R Rozof
(74) *Attorney, Agent, or Firm* — Cantor Colburn LLP (57) ABSTRACT

The invention provides a new compound, a method to produce it and use of it as an antimicrobial agent, as well as pharmaceutical compositions comprising it. It is also disclosed use of actinomycetes bacteria to produce the compound (Formula III).

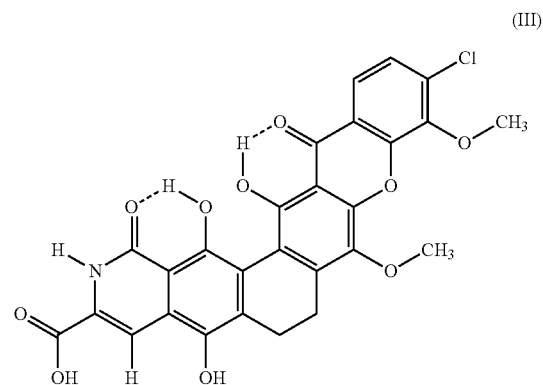

19 Claims, 2 Drawing Sheets
Specification includes a Sequence Listing.

Figure 1: LC-DAD-isoplot (upper) and MS spectra at ESI+ (middle) and MS spectra of ESI- (bottom) of the active fraction of the MP127-ig17 extract fractionated on HPLC.

Figure 2: Key NMR and MS data supporting the structure og MBL-AB01.

ANTIMICROBIAL COMPOUND

CROSS REFERENCE TO RELATED APPLICATIONS

This application is a National Stage application of PCT/EP2017/059521, filed Apr. 21, 2017, which claims the benefit of NO 20160680, filed on Apr. 22, 2016, both of which are incorporated by reference in their entirety herein.

The invention provides a new compound, a method to produce it and uses as an antimicrobial agent.

BACKGROUND

Natural products remain the most prolific source of new antimicrobials, and the chemical diversity of natural compounds is still unmatched by combinatorial chemistry approaches (Newman and Cragg, 2012). While the latter has been successfully applied for lead optimization, it basically failed to deliver genuinely new pharmacophores, especially in the field of antimicrobials. This is mainly due to limitations in the structural variety of compounds represented in combinatorial libraries. Most of the antibiotics in clinical use today have been developed from compounds isolated from bacteria and fungi, with members of the actinobacteria being the dominant source (Peláez F, 2006). Actinobacteria-derived antibiotics that are important in medicine include aminoglycosides, anthracyclines, chloramphenicol, macrolides, tetracyclines, etc. Traditionally, most of these antimicrobials have been isolated from soil-derived actinomycetes of the genus Streptomyces.

However, isolation strategies in recent years have been directed to unexploited environments like marine sources. Bioprospecting efforts focusing on the isolation and screening of actinobacteria from ocean habitats have added new biodiversity to the order Actinomycetales and revealed a range of novel natural products of potential pharmacological value (Mincer 2001). The existence of marine actinobacterial species that are physiologically and phylogenetically distinct from their terrestrial relatives is now widely accepted, and new taxonomic groups of marine actinomycetes have been described for at least six different families within the order Actinomycetales (Fenical et al 2006).

Apart from being phylogenetically distinct from their terrestrial relatives, marine isolates have been shown to possess specific physiological adaptations (e.g., to high salinity/osmolarity and pressure) to their maritime surroundings. The immense diversity of this habitat along with its underexploitation is the fundamental reason for attracting researchers toward it for discovering novel metabolite producers. There is an occurrence of distinct rare genera in the marine ecosystem, and many were found to produce novel and chemically diverse secondary metabolites (Riedlinger 2004), (Zotchev, 2012), (Manivasagan et al., 2014).

Most streptomycetes and other filamentous actinomycetes possess numerous gene clusters for the biosynthesis of secondary metabolites (Bentley et al 2002), and genome sequence studies have revealed that large portions of their genomes are devoted to secondary metabolite biosynthesis. Several gene clusters coding for known or predicted secondary metabolites has been identified in the genome of different Streptomyces strains (Brautaset et al 2003), and the marine actinomycete Salinispora (Bode et al, 2002). Many medicinally important natural products, including antibacterials and antifungals, are synthesized by these multimodular assembly lines, and genome mining for secondary metabolite gene clusters has become a common tool to assess the genetic capability of bacteria to produce novel bioactive compounds (Fischbach and Walsh, 2006).

However, even for well-studied model antibiotic producers like Streptomyces coelicolor A3(2), discrepancies between the number of known metabolites on the one hand and the number of pathways identified from genomic data on the other hand are tremendous (Bentley et al 2002). These discrepancies can only be explained by the facts that most gene clusters for secondary metabolites are silenced under standard laboratory cultivation conditions and that an expression or upregulation of these pathways is only triggered in response to certain environmental signals. It has been shown that by cultivating bacteria under a range of conditions, it is possible to obtain products of many of these "orphan" biosynthetic pathways (Bode, 2002).

In Engelhardt et al (2010), twenty-seven marine sediment- and sponge-derived actinomycetes were classified at the genus level using molecular taxonomy. As described, PCR-screenings for genes involved in polyketide and non-ribosomal peptide antibiotic synthesis was used for analyzing the actinomycetes potential to produce bioactive secondary metabolites.

Most of the antibiotics in clinical use today were discovered more than 5 decades ago. Over the last 10 years, only two new antibacterial agents with new mechanisms of action (the synthetic oxazolidinone linezolid and the natural-product-based lipopeptide daptomycin) have been approved. Loss of efficacy of existing drugs due to emerging multidrug resistant pathogens threatens to outpace the development of new antimicrobials. The majority of all anti-infective drugs are either derived from or inspired by natural products. Accordingly, new antibiotics are most likely to come from natural product-based research since neither genomics-derived target based research nor combinatorial chemistry has so far provided drugs that have actually entered the market.

Thus, mining microbial diversity represents the most promising source for obtaining new and diverse antimicrobial leads to meet the challenges with emerging multidrug-resistance.

SUMMARY OF INVENTION

The invention provides a new compound, having the structure according to formula III.

(III)

and derivatives, salts and solvates thereof.

A method for producing the compound is also provided comprising the following steps:
a) cultivating a bacterium selected from the group consisting of:

i) a bacterial isolate deposited under the Budapest Treaty with Leibniz-Institut DSMZ-Deutsche Sammlung von Mikroorganismen and Zellkulturen GmbH, InhoffenstraBe 7B, 38124 Braunschweig, Germany (hereinafter denoted DSMZ) on date Apr. 7, 2016 under deposit number DSM 32287; and ii) a bacterium which is closely related to the bacterial isolate in i) such as a strain with similar genotypic and/or phenotypic characteristics to the isolated bacterium;

in a suitable culture medium comprising sea water;

b) extracting the compound of claim 1 from the culture.

In one embodiment of the method for producing the compound the bacterium is a bacterium which comprises in its genome a 16S rRNA which by reverse transcription and $2^{nd}$ strand synthesis provides a sequence which is at least 80% identical to the sequence depicted in SEQ ID NO 1.

Further it is specified that step b) of the method may comprise centrifugation of the cultivated bacteria to obtain a cell pellet, from which the compound is extracted, and the step of extracting the compound from the cell pellet using dimethyl sulfoxide (DMSO).

In one embodiment the culture medium is PM6, optionally with artificial sea water.

It is also provided use of an isolated bacterium to produce the compound according to claim 1, wherein the bacterium is selected from the group consisting of:

i) a bacterial isolate deposited under the Budapest Treaty with DSMZ on date Apr. 7, 2016 under deposit number DSM 32287; and b) a bacteria which is closely related to the bacterial isolate of a) such as a bacterium with similar genotypic and/or phenotypic characteristics to the isolated bacterium.

It is further provided use of isolated bacteria wherein it is specified that the closely related bacterium comprises in its genome a 16S rRNA which by reverse transcription and $2^{nd}$ strand synthesis provides a sequence which is at least 80% identical to the sequence depicted in SEQ ID NO 1.

Another aspect of the invention is a pharmaceutical composition comprising the compound of the invention, and pharmaceutically acceptable one or more carriers and/or excipients, and the compound for use in therapy, such as an antimicrobial agent, more specifically an antibacterial agent.

Another embodiment of the invention is a method for treating a bacterial infection in a subject comprising administering the compound of the invention or the pharmaceutical composition to said subject.

According to yet another embodiment, the bacterial infection is caused by a multidrug resistant bacterium, such as a Gram-positive and/or Gram-negative bacterium multiresistant bacterium.

Yet another aspect of the invention is a method for killing or inhibiting the growth of a bacterium comprising the step of bringing the compound of the invention or the pharmaceutical composition in contact with the bacteria to be killed or inhibited.

The invention also includes non-medical use of the compound as antibacterial agent.

DETAILED DESCRIPTION

The present invention provides a new antimicrobial agent. The inventors have analyzed marine sediment-derived actinomycete isolates, thereby identifying new bacteria able to produce antimicrobial secondary metabolites.

By using microwell, shake flask and fermenter cultures, the inventors were able to identify culturing conditions for the production of antibacterial and antifungal compounds. The approach led to the identification of a new antimicrobial compound, MBL-AB01.

Accordingly, the invention provides a new antimicrobial compound, such as MBL-AB01.

Compounds like MBL-AB01 belong to a group of compounds produced by microorganisms often referred to as secondary metabolites.

By "secondary metabolites", we mean compounds that the microorganisms can synthesize. They are not essential for basic metabolic processes, such as growth and reproduction. Secondary metabolites may have other useful characteristics, such as anti-cancer and/or antimicrobial activity, such as anti-fungi and anti-bacterial activity (Behal, 2000; Bennett and Bentley, 1989)

Structure elucidation of the compound MBL-AB01 has revealed that the compound is a new compound belonging to the Xanthon class of compounds. The molecular formula is as shown in formula I:

Molecular formulae: $C_{27}H_{18}ClNO_{10}$     (I)

A general molecular structure of the present compound is shown in formula II:

$R_1$ may be a halogen atom, selected from chlorine, bromine and iodine, $R_2$ and $R_3$ may be —O—$CH_3$. $R_4$ may be —COOH, —C(O)$OR_1$ and —C(O)$NR_1R_2$, and $R_1$ and $R_2$ are independently a hydrogen, a $C_1$-$C_4$-alkyl group, a $C_2$-$C_4$-alkenyl group, a $C_2$-$C_4$ alkynyl group and a phenyl group.

The compound according to the invention is a xanthon compound with the general structure formula II.

In one embodiment, the invention has the molecular formula I and the structure as shown in formula III, and derivatives, solvates and/or hydrates thereof.

(III)

A former known compound, Xantholipin, has the same molecular formula as depicted in formula I. However, a comparison of the structure revealed significant differences between the molecules Xantholipin and the invention MBL-AB01. The differences are summarized below:

|  | Xantholipin | MBL-AB01 |
|---|---|---|
| No. of labile hydrogens | 3 | 5 |
| Predicted logP | 2.6 | 4.8 |
| Chiral centers | 3 | 0 |
| Lowest predicted pKA | 9.0 | 2.9 |

The invention is a compound having a structure according to the formula III, and derivatives, solvates and/or hydrates thereof. As provided by the invention, derivatives is compounds with a structure according to formula II, where $R_1$ is a halogen atom, selected from chlorine, bromine and iodine, $R_2$ and $R_3$ is —O—$CH_3$. $R_4$ is —COOH, —(O)$OR_1$ and —C(O)$NR_1R_2$, and $R_1$ and $R_2$ are independently a hydrogen, a $C_1$-$C_4$-alkyl group, a $C_2$-$C_4$-alkenyl group, a $C_2$-$C_4$ alkynyl group and a phenyl group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

The new antibacterial compound according to the invention is produced by actinomycete bacteria, such as a strain in the genera *Actinalloteichus*. In one particular embodiment the antibacterial compound of the invention is produced by culturing of the marine sediment-derived bacterial isolate MP127-ig17 or closely related strains.

By "closely related strains", we mean any strain that shares similar genotypic and/or phenotypic characteristics to the isolated strain. In particular, this phrase encompasses slightly modified forms of the strain that retain substantially the same functional activities. Thus, for example some amino acid or nucleotide additions, deletions or alterations have very little effect; if any, on the functional ability to produce a compound according to the invention. A definition of the term "closely related strains" is provided in Peak et al, which may be used herein.

Further, the invention provides a method for producing an antimicrobial agent, such as MBL-AB01, comprising the step of cultivating actinomycetes bacteria, such as a strain in the genera *Actinalloteichus*. In one particular embodiment the compound is produced by a bacterium selected from the group consisting of i) a bacterial isolate deposited under the Budapest Treaty with DSMZ on date 7 Apr. 2016 under deposit number DSM 32287; and ii) a bacterium which is closely related to the bacterial isolate of i) such as a bacterium with similar genotypic and/or phenotypic characteristics to the isolated bacterium.

The compound-producing bacterium, as described herein, may be a bacterium which comprises in its genome a 16S rRNA which by reverse transcription and 2nd strand synthesis provides a sequence which is at least 80% identical, such as at least 82%, 83%, 85%, 86%, 87%, 90%, 91%, 92%, 93%, 94%, 95%, 96%, 97%, 98%, 98.5%, 98.7%, 98.8% or 98.9% or 99% identical, to the sequence set forth in SEQ ID NO: 1.

The skilled person will expect that considerable alterations may be introduced into a sequence defined in SEQ ID NOs: 1 and subsequences thereof without significantly altering its overall structure, function and properties.

By "phenotypic characteristics", we mean the ability to produce the secondary metabolite according to the invention, i.e the compound with a molecular structure according to any one of formula II and/or III.

By "genotypic characteristics", we mean characteristic features of genetic molecules such as nucleic acids and amino acids, such as the 16S rRNA molecule, for example known as sequence identity. As referred to herein "strains with similar genotypic characteristics" include bacteria comprising a 16S rRNA which by reverse transcription and 2nd strand synthesis provides a sequence which is at least 80% identical, such as at least 82%, 83%, 85%, 86%, 87%, 90%, 91%, 92%, 93%, 94%, 95%, 96%, 97%, 98%, 98.5%, 98.7%, 98.8% or 98.9% or 99% identical, to the sequence set forth in SEQ ID NO: 1.

The expression "bacterial isolate" is often used to define a culture of one bacterial strain. The isolate may be purified and isolated by different means known to the skilled person in the art. A "bacterial isolate" or "bacterial strain", as used herein, refers to a genotypic and phenotypic unique microorganism, traceable back to a colony, typical derivable from blotting a purified sample into a suitable medium. The expressions isolate, strain and bacterium are used interchangeably.

According to the method of the invention, the bacteria are cultivated in a microbiological culture with a suitable culture medium, known to the skilled person. In one embodiment, the culture medium comprises sea water.

A "microbiological culture", or microbial culturing, is a method of multiplying microbial organisms by letting them reproduce in predetermined culture media under controlled laboratory conditions. The term "culture" is more generally used informally to refer to "selectively growing" a specific microorganism as a bacterium in the lab.

The compound according to the invention is obtainable from a bacterial culture as described herein.

Accordingly, the invention provides a method for producing the compound of formula III, and derivatives, solvates and/or hydrates thereby, by cultivating bacteria as described herein in a culture with a suitable culture medium.

In one embodiment the culture medium is a commercially available growth medium commonly used for culturing bacteria, such as Trypton Soya broth (Oxoid). In another embodiment, the culture medium is a standard culture medium such as Luria-Bertani (LB) medium. Yet another embodiment is a complex medium designed for production of secondary metabolite by Actinomycetes such as PM6 described in Engelhardt et al., 2010. In yet another embodiment the culture medium is supplemented with artificial seawater. In one embodiment, an inoculum culture with the compound-producing bacterial strain is produced in flasks filled with trypton soya broth medium with seawater.

The culture comprising the cultured bacteria may optionally be a production culture. The production cultures may be inoculated from seed cultures. The production cultures may be produced in flasks filled with a suitable culture medium, such as PM6 medium with artificial seawater.

By "suitable culture medium", we mean any medium known to the skilled person suitable to grow the bacterium in question. As used herein, the expressions "culture medium" or "fermentation medium" or "cell culturing" refer to a nutrient solution used for growing and shall refer to all kinds of media which are used in the context of culturing the isolates. Typically, a culture medium comprises a carbon source such as sugars, starch, flour or yeast extract, a nitrogen source such as flour containing proteins and amino acids or ammonium sulphate and minerals such as inorganic salts.

The culture media may be chemically defined such as MR6 (Illing et al., 1989), complex media such as PM4, PM5 and PM6 described in Engelhardt et al., 2010 or standard culture media such as ISP2. Other typical examples of culture media for the production of antibiotic compounds are R2YE (Thompson et al., 1980), R5 (Illing et al., 1989) and AMP (Wendt-Pienkowski et al., 2005).

The method of the invention further comprises the step of isolating the antibacterial compound from the culture. The isolation of the compound from the cultured bacteria may be done by means well known to the skilled person.

One method of obtaining the compound is by extracting it from the production culture and/or from the cell pellet that is collected by centrifugation of the production culture. This may be done by harvesting the dry matter that is collected by centrifugation of the culture. Optionally the dry matter can be washed with methanol to extract compounds that are not related to the active compound.

The compound may be extracted by a suitable solvent known to the skilled person.

In one particular embodiment, the dry matter from the production culture may be collected by centrifugation and optionally fractionated or lysed by means familiar to the skilled person, for example by freeze-drying the cell pellet.

Further, the compound may be extracted by a suitable solvent, such as by DMSO or DMSO added trifouoroacetic acid (TFA) to 0.1%. The compound may also be extracted by other organic solvents such as alcohols and alkanes. Undissolved matter is optionally removed by filtration. In one embodiment, the compound is further separated by chromatography, such as HPLC. One embodiment the separation is done by HPLC at basic conditions.

To optionally avoid degradation of the compound, pH of the fractions can be adjusted, for example by adding a buffer, such as an ammonium acetate buffer with pH=4, to each of the fraction collector vials prior to fractionation. The active compound in the fractions is further bound to a solid phase column, conditioned with an alcohol, such as methanol, optionally acidified with ammonium acetate buffer at pH=4. After the compound is bound to the column, impurities are washed out of the column with acidified alcohol, such as methanol.

The compound is further eluted from the column with an alcohol, such as methanol, optionally also added ammonium acetate buffer pH adjusted to pH=8.0. Further, the method of isolating the compound may comprises the step of removing the alcohol or other solvents by vacuum centrifuge, before the compound is added water and freeze-dried.

A method for identifying the compound of the invention is by use of high-performance liquid chromatography (HPLC), such as HPLC-MS or HPLC-UV and high resolution mass spectroscopy (MS).

In Engelhardt et al (2010), an isolation process of marine actinomycete bacteria is described. The study provided the molecular taxonomy and phylogenetic analyses of 27 different actinomycete bacteria. In table 1, one isolate referred to as TSI127-17 derived from sponge is described. Sequence analyses of the 16S rRNA gen revealed that TSI127-ig17 had a 98.97% gene similarity to the *Actinoalloteichus hymeniacidonis* HPA177 with GenAccession no. DQ144222. In Engelhart et al. (2010), PCR screening for PKS/NRPS genes was used to investigate the potential of these actinomycete isolates to synthesize polyketide- and nonribosomal peptide-derived secondary metabolites, thus indicating the potential of these actinomycetes isolates to synthesize secondary metabolites.

Herein, the deposited bacterium (DSM 32287) is provided comprising in its genome a 16S rRNA molecule having the sequence depicted in SEQ ID NO 1.

An aspect of the invention is the use of new bacterial isolates of actinomycete bacteria to produce an antimicrobial compound as MBL-AB01.

Thus, the invention is use of a bacterium in the genera *Actinalloteichus* to produce secondary metabolites, such as the antimicrobial compound MBL-AB01. The bacteria to be used may be the antimicrobial compound-producing strain *Actinalloteichus hymeniacidonis*.

In a particular embodiment, the bacteria according to this aspect of the invention is the bacterial isolate (DSM 32287) designated MP127-ig17, or closely related strains, as defined herein. In another particular embodiment, the invention is the use of a bacterium selected from the group consisting of i) a bacterial isolate deposited under the Budapest Treaty with DSMZ on date 7 Apr. 2016 under deposit number DSM 32287; and ii) a bacterium which is closely related to the bacterial isolate of i) such as a bacterium with similar genotypic and/or phenotypic characteristics to the isolated bacterium to produce secondary metabolites, such as compounds having a structure according to any one of the formula I and/or II and/or III, and derivatives, solvates and/or hydrates thereof with the same functional properties as MBL-AB01.

The compound-producing bacterium, as described herein, may be a bacterium which comprises in its genome a 16S rRNA which by reverse transcription and 2nd strand synthesis provides a sequence which is at least 80% identical, such as at least 82%, 83%, 85%, 86%, 87%, 90%, 91%, 92%, 93%, 94%, 95%, 96%, 97%, 98%, 98.5%, 98.7%, 98.8% or 98.9% or 99% identical, to the sequence set forth in SEQ ID NO: 1. The structural and biological features of the new antimicrobial compound, MBL-AB01, have been characterized. It has been shown that the compound of the invention is a powerful antibacterial agent shown to inhibit growth of a variety of bacterial strains, including multidrug resistant bacteria.

The antibacterial activity has been determined by in vitro studies, such as described in Example 5.

It has also been demonstrated in vitro that MBL-AB01 is less cytotoxic than comparable compounds such as Xantholipin, as described in Example 6. Thus, MBL-AB01 is a very attractive candidate as an antimicrobial agent, useful in different pharmaceutical compositions.

Accordingly, the invention also provides the use of the compound of the invention in medical applications, such as in therapy. The invention includes a compound of the formula I and/or II and/or III, or a pharmaceutically acceptable salt or solvates thereof, for use in therapy, in particular for the treatment of bacterial infections.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The compounds of the invention and pharmaceutically acceptable salts or solvates thereof may be used on their own but will generally be administered in the form of a pharmaceutical composition in which the compound/salt/solvate (active ingredient) is in association with pharmaceutically acceptable excipients, diluents or carriers. Such pharmaceutical compositions are provided by the invention.

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, a-ketoglutarate, and 0-glycerophosphate. Suitable inorganic salts may also be formed, including hydrochloride, halide, sulfate, nitrate, bicarbonate, and carbonate salts (Berge et al 1997).

Thus, the invention provides a pharmaceutical composition comprising a compound of the formula I and/or II and/or III, or a pharmaceutically acceptable salt or solvates thereof. Such composition is useful in the treatment of different microbial infections.

The present invention further relates to compositions comprising the strains, culture broth, culture media, inoculum, extracts, cell pellet, or compounds of formula I and/or II and/or III and their salts of the invention, as well as to their use for protection against infections by harmful microorganisms, and to corresponding methods which comprise treating animals, including humans, against microbial infections with an effective amount of the compositions, strains, culture broth, culture media, inoculum, extracts, cell pellet, or compounds of formula I and/or II and/or III and their salts or solvates of the invention.

As used herein, "composition" in reference to a product (microbial strain, agent, compound or formulation) of the present invention refers to a combination of ingredients, wherein "formulating" is the process of using a formula, such as a recipe, for a combination of ingredients, to be added to form the formulation. Such composition may also be referred to as formulation. The strains, culture broth, culture media, inoculum, extracts, cell pellet, or compounds of formula I and/or II and/or III, and compositions of the invention, respectively, are suitable as antimicrobial agents or antibiotics.

The invention further include a kit comprising an isolated bacterial culture having accession number DSM 32287, the strains, culture broth, culture media, inoculum, extracts, cell pellet, or compounds of formula I and/or II and/or III and their salts of the invention. A kit comprising the isolated bacterial culture, the strains, culture broth, extracts, cell-free extracts, culture media, inoculum, or compounds of formula I and/or II and/or III and their salts of the invention, is useful for treating a broad spectrum of bacterial infections.

The invention still further provides a process for the preparation of a pharmaceutical composition of the invention, which comprises mixing a compound of either one of the formula I, II, and/or III or a pharmaceutically acceptable salt or solvate thereof with a pharmaceutically acceptable diluent, excipient or carrier. The skilled person will be able to identify suitable pharmaceutical excipients dependent upon the administration route.

The compound for use as a medicament, such as an antimicrobial agent, more specifically an antibacterial agent, is provided.

The in vitro antibacterial activity of the invention was determined against a panel of bacterial strains. As shown in the examples, a compound according to the invention is active against multiresistant Gram-positive bacterial, including vancomycin-resistant *Enterococcus faecium*.

The use of a bacterium, such as the deposited bacterium isolate or a closely related strain, for producing the compound is also provided.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like. The infection can be a bacterial infection, for example, one caused by a bacterium described herein. A method for killing or inhibiting the growth of a bacterium is also provided, comprising the step of bringing the compound according to the invention into contact with the bacterium to be killed. This method may additionally comprise the step of contacting the bacterium with a pharmaceutical composition as described herein.

The ability of a compound of the invention to treat a bacterial infection may be determined by using assays well known to the art. For example, the design of treatment protocols, toxicity evaluation, data analysis, quantification of cell kill, and the biological significance of the use of antibacterial screens are known. In addition, ability of a compound to treat a bacterial infection or kill or inhibit bacteria may be determined using the assays as described herein.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated.

The term "about" can refer to a variation of ±5%, ±10%, ±20%, or ±25% of the value specified. For example, "about 50" percent can in some embodiments carry a variation from 45 to 55 percent.

As will be understood by the skilled person, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

EXAMPLES

Example 1: Isolation of MP127-ig17

Isolation and Taxonomy of MP127-Ig17

The isolation of a bacterial isolate belonging to *Actinoalloteichus hymeniacidonis* (TS1127-17) has been described previously (Engelhardt et al., 2010).

Shortly, sponge samples were collected from the Tautra ridge (63°36'53"N, 10°31'22"E, Trondheim Fjord, Norway) at 60 m depth. Homogenized material was plated on different agar medium, and the isolate, denoted MP127-ig17, was isolated from agar medium IM18: 3 g/l crab flour, 2 g/l sea weed flour, 20 g/l agar, pH 8.0, prepared with 0.5× natural sea water and 1 ml/l vitamin B solution (5 mg/l each of thiamine-HCl, riboflavin, niacin, pyridoxin-HCl, inositol, Ca-pantothenate, p-aminobenzoic acid, 2.5 mg/l biotin). MP127-ig17 did not grow on this medium in the absence of sea water.

Sequencing of the 16S rDNA showed 98.97% gene similarity to *Actinoalloteichus hymeniacidonis* HPA177.

MP127-ig17 has been de deposited under the Budapest Treaty with DSMZ on date Apr. 7, 2016 under deposit number DSM 32287.

Screening for Bioactivity

The isolates from the sponge sample were cultivated in different production media at 25° C., and extracts were screened using agar diffusion assay as described previously (Engelhardt et al., 2010). The isolate designated MP127-ig17 was cultivated in PM6 medium (soluble starch 10 g/l; yeast extract 2 g/l; glucose 10 g/l; glycerol 10 g/l; cornsteep powder 2.5 g/l; peptone 2.0 g/l; CaCO3 3.0 g/l) with 25% 2× artificial sea water. 2× artificial sea water was prepared as follows: 1.34 g/l KCl, 2.72 g/l $CaCl_2 \times 2H_2O$, 12.58 g/l $MgSO_4 \times 7H_2O$, 9.32 g/l $MgCl_2 \times 6H_2O$, 0.36 g/l sodium bicarbonate, pH=7.8. The solution was sterilized by filtration.

It was shown that the extracts of MP127-ig17 were able to inhibit growth of *Micrococcus luteus* ATCC9341, *Enterococcus faecium* CCUG37832, *Candida albicans* ATCC10231 and *Candida albicans* CCUG39434.

Example 2: Identification of Bioactive Compound, MBL-AB01

Inoculum of MP127-ig17 was produced in 500 ml shake flasks filled with 100 ml trypton soya broth medium (Oxoid) with 0.5× artificial sea water. The culture was incubated at 30° C. for 5 days. Production cultures were inoculated (3%, vol/vol) from seed cultures. The production was performed in 500 ml shake flasks filled with 125 ml PM6 medium with 0.5× artificial seawater. The culture was incubated at 25° C. for 12 days. The culture was freeze dried and extracted with DMSO.

The DMSO extract was fractionated on an Agilent 1100 series high-performance liquid chromatography (HPLC) system with a Zorbax Bonus-RP column (2.1×50 mm, 3.5 μm) connected to a diode array detector (DAD) and a fraction collector system. Methanol and 10 mM ammonium acetate (pH 4) were used as the mobile phase, and the methanol gradient was linearly increased from 10 to 90% for 24 min. Fractions were sampled every minute for the whole run. The fractions were dried in a vacuum centrifuge and re-dissolved in DMSO.

The fractions were tested for activity in a robotic liquid based bioassay with *Micrococcus luteus* ATCC9341 and *Enterococcus faecium* CCUG37832 as indicator organisms. Active fractions were analyzed on an Agilent HPLC system with a Zorbax Bonus-RP column (2.1 by 50 mm, 3.5 μm) connected to a DAD and a time-of-flight (TOF) apparatus to determine the accurate mass of the bioactive compound. 10 mM ammonium acetate (pH 7) and acetonitrile were used as the mobile phases, and electrospray ionization was performed in the negative mode.

Figure 1:
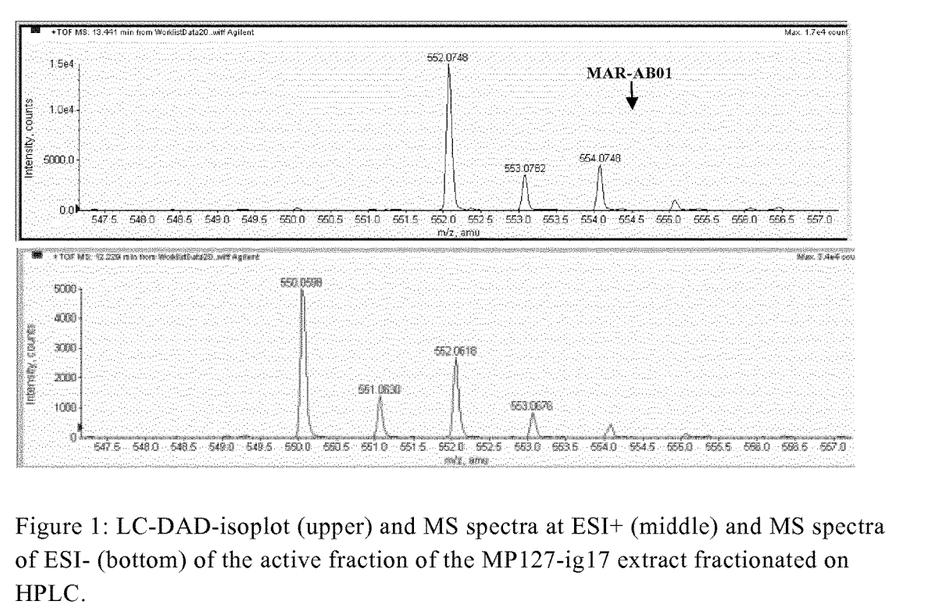
FIG. 1 shows LC-DAD-isoplot (upper spectre) and MS spectra at ESI+ (middle) and MS spectra of ESI− (bottom) of the active fraction of the MP127-ig17 extract fractionated on HPLC.

An UV abortion peak at 395 nm in the active fraction correlated with peeks in LCMS Q-Tof chromatograms with positive and negative electrospray ionization consistent with the molecular mass of MBL-AB01. After obtaining the correct molecular structure the molecular mass has been calculated to 551.061927. The spectra are shown in FIG. 1.

Example 3: Characterization of Active Compound, MBL-AB01

Isotope Labelling and Determination of Molecular Formula

The molecular formula of MBL-AB01 was determined by production in media with $^{13}C$, $^{15}N$ or $^{13}C$ and $^{15}N$ labeled compounds. Seeds were produced in a two stage cultivation. First, MP127-ig17 was inoculated in TSB broth supplemented with 50 sea water and incubated for 4 days, then the seed were re-inoculated in *E. coli*-OD2 medium with wither $^{13}C$, $^{15}N$ or $^{13}C+^{15}N$ labeling (Silantes) supplemented with 50% sea water and incubated for 6 days. Seeds were transferred to production media with the following composition: *E. coli*-OD2 medium with wither $^{13}C$, $^{15}N$ or $^{13}C+^{15}N$ labeling (Silantes); 537 ml/l, unlabeled or $^{15}N$ labeled $(NH_4)_2SO_4$; 0.34 g/l, $MgSO_4 \times 7H_2O$; 0.17 g/l, $CaCO3$; 2.1 g/l, $KH_2PO_4$; 0.086 g/l, unlabeled or $^{13}C$ labeled glucose; 10 g/l, TMST (Olga Sekurova Håvard Sletta 1999); 1.3 ml/l and incubated for 11 days. The culture was freeze dried, extracted with DMSO and analyzed as described above. The mass in negative mode (M-H) of unlabeled, $^{13}C$ labeled, $^{15}N$ labeled and $^{13}C$ and $^{15}N$ labeled MBL-AB01 was 550.05, 577.05, 551.05 and 578.14 respectively. Thus, the increased atomic mass due to $^{13}C$ and $^{15}N$ labeling demonstrates that MBL-AB01 has 27 carbons and 1 nitrogen.

Determination of Molecular Formula and Structure Elucidation with FT-ICR

Characterization of MBL-AB01 was performed by direct infusion into a Bruker Solarix 12T FT ICR MS equipped with an ESI source. MS spectra were recorded in positive and negative ESI mode. The most abundant ions in the spectra were isolated and fragmented by CID. Mass calibration was performed externally using an NaTFA standard. The sample was diluted in methanol/water.

The Bruker Compass Data analysis software was used to predict possible molecular formula compositions for the ions detected. The prediction was performed allowing for the presence of C, H, N, O for all ions. In addition other elements; S, Br, Cl, P, etc. were included in searches for which the isotope pattern suggested the presence of other atoms than C, H, N, and O. The prediction was initially performed allowing for 2 ppm mass error. Theoretical isotope patterns of the suggested molecular formulas were compared to the signals in the MS spectra. HDX analyses were performed by diluting a sample of MBL-AB01 in d4-methanol, and CID spectra were recorded after 60, 120 min and 240 hours.

The isotope pattern shows the presence of Cl. The molecular formula was identified as $C_{27}H_{18}ClNO_{10}$ and this formula is consistent with the results form the fermentation labeling experiment and the isotopic distribution observed with both LC-QTOF and FT-ICR. Fragmentation experiments show the loss of $CO_2$ followed by water from the suggested molecular ion. The HDX analyses show the presence of a maximum of 5 exchangeable protons.

Structural Elucidation with NMR

The aim was to identify the chemical structure of the molecule identified as the active compound in Example 2, with a mass of 551.061927 Da, and the chemical formula of $C_{27}H_{18}ClNO_{10}$. Xantholipin is the only molecule disclosed in the public domain with this chemical formula, but data clearly show that MBL-AB01 is not identical to Xantholipin.

A vial of 0.7 milligram of purified MP127-ig17 was obtained. The solid material was stored at −18° C. until the NMR experiments were.

The sample was dissolved in 120 μl DMSO-d6 in the vial. The solution was transferred to a 3 mm NMR sample, PN027-20-02. An additional 60 μl of DMSO-d6 was used to rinse the vial and this washing solution was also transferred to the NMR tube. The tube was flushed with nitrogen gas before the cap was put on. NMR experiments were performed on the 800 MHz spectrometer with a TCO cryoprobe ($^{13}C$ inner coil, i.e. optimized for carbon detection).

Figure 2:
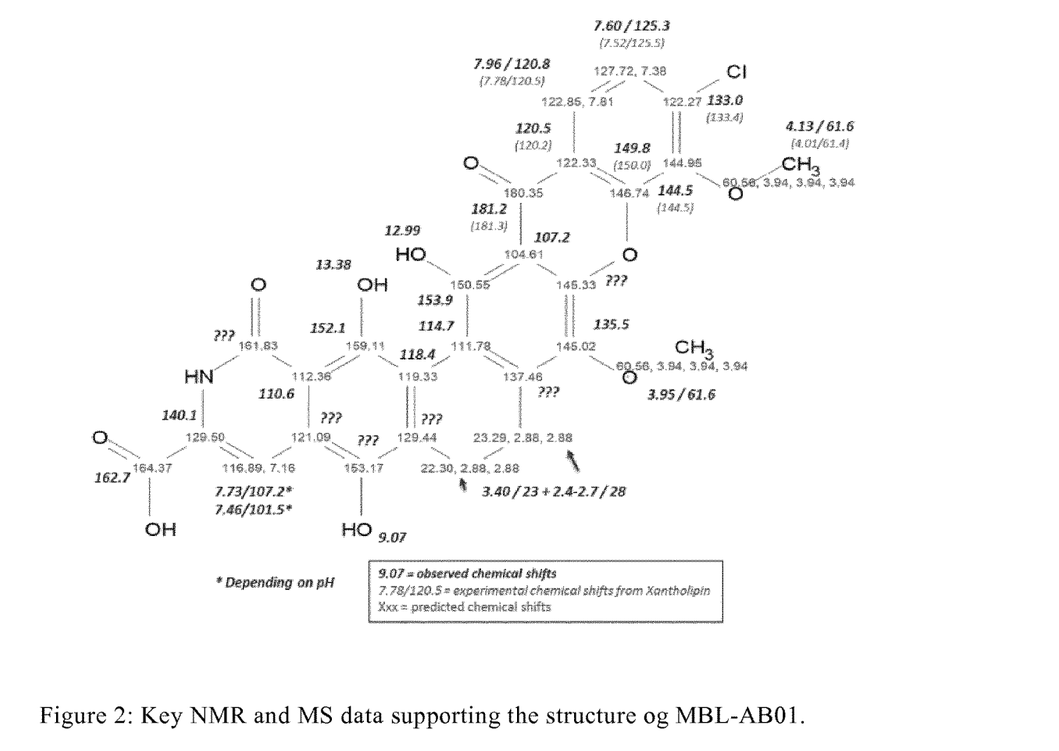
FIG. 2 shows the structur of MBL-AB01 with key NMR and MS data supporting the structure.

The 1D $^1H$ spectrum revealed a very pure sample of MBL-AB01. The sample was further analyzed by a number of additional NMR spectra (see FIG. 2).

The proposed structure of MBL-AB01 (see formula III) is supported by and consistent with all NMR and MS data available. The structure is also considered reasonable with respect to data and publications on biosynthetic pathways of related compounds (e.g. Xantholipin) as well as fully realistic from a general organic chemistry perspective.

(III)

Example 4: Isolation of the Active Compound from Bacterial Culture with 0.5× Artificial Sea Water Cultivation of MP127-ig17 for the production of MBL-AB01 was performed in 3-liter Applicon fermentors with 1.65 liter PM6_MOD3 media in batch fermentation (The composition of the PM6_MOD3 media used: soluble starch 30 g/l; yeast extract 2 g/l; cornsteep liquor 2.5 g/l; peptone 2.0 g/l; CaCO3 3.0 g/l). Fermentations were run for 8 days at 25° C. with 0.25 vvm aeration (gas volume flow per unit of liquid volume per minute) from start, then reduced to 15 vvm for the rest of the cultivation and agitation. Dissolved oxygen was above 30%. Seed cultures for the fermentations were prepared in 500-ml baffled shake flasks with 100 ml tryptone soy broth medium (Oxoid).

The dry matter from PM6_MOD3 fermentation broth was collected by centrifugation and then freeze dried. The resulting powder was then washed with 50 ml methanol/g powder and the extracted twice with 5 and 10 ml DMSO/g powder respectively. The two DMSO extracts were mixed and then freeze dried. The dried extract was resuspended in a small amount of DMSO, and undissolved matter was removed by filtration.

The extract was separated on an Agilent HPLC system with a Zorbax eclipse XBD-C18, 5 μm, 9.4×250 mm column connected to a diode array detector and a fraction collector. 20 mM ammonium acetate added 0.4 ml 25% $NH_3$/l [A] and methanol were used as mobile phases. The HPLC was run isocratic at 76% [B] for the first 7.5 min. From 7.6 to 9.0 min 100% [B] was applied. The active compound eluted at approximately 5.5 min. To avoid degradation of the compound, 0.01× the fraction volume of 50 g/l ammonium acetate pH=4 was added to each of the fraction collector vials prior to fractionation. The active compound in the fractions was bound to a solid phase column (60 mg Oasis HLB) that was conditioned with 100% methanol, then 76% methanol added 0.1% 50 g/l ammonium acetate pH4. After the compound was bound to the column, the column was washed with 1.5 ml 85% methanol pH=4, then with 5 ml 76% methanol pH=4. The compound was eluted from the column with methanol added 0.1% of 50 g/l ammonium acetate pH=8. Methanol was removed in a vacuum centrifuge; the compound was added water and freeze dried.

Example 5: In Vitro Antibacterial Activity (MIC Determination) of MBL-AB01, a Comparison with Other Known Antimicrobial Compounds MBL-AB01 was tested against a panel of Gram-negative and Gram-positive pathogens. MICs for all Gram-positive and Gram-negative bacterial strains were determined by standardized microdilution tests using Mueller-Hinton broth (Acumedia). Bacterial inoculums containing $5×10^5$ CFU/ml were incubated for 19 h at 35° C. in the presence of different antibiotic concentrations according to Clinical and Laboratory Standards Institute protocols. The bacterial strains were obtained from the culture collections ATCC (American Type Culture Collection), NCTC (National Collection of Type Cultures) and CCUG (culture collection university of Göteborg Sweden).

The MICs of MBL-AB01, ranging from below 0.032 to 0.5 μg/ml for most Gram-positive strains, were comparable to or lower than those of the reference antibiotic vancomycin, gentamicin, streptomycin and daptomycin (Table 1). MBL-AB01 also inhibited the growth of vancomycin-resistant bacterial strains represented by *Enterococcus faecalis* CCUG 37832 and *E. faecium* CTC 492, with a MIC of 0.25 and 0.5 μg/ml, respectively.

TABLE 1

In vitro antibacterial activity of compound MBL-AB01 against different bacterial strains.

| | MIC μg/ml | | | | |
|---|---|---|---|---|---|
| | MBL-AB(+)01 | Vancomycin | Gentamicin | Streptomycin | Daptomycin |
| *E. faecium* CCUG 37832* | 0.25 | >16 | 16 | >16 | >16 |
| *E. faecium* CTC 492 | 0.5 | 1 | 16 | >16 | >16 |
| *M. luteus*, ATCC 9341 | 0.063 | 1 | 4 | 8 | 0.5 |
| *S. aureus* ATCC 29213 | <0.032 | 2 | 4 | 16 | 4 |
| *S. aureus* ATCC 43300 (MRSA) | 0.032 | 2 | 16 | 16 | 4 |
| *S. aureus* NCTC 6571 | 0.032 | 2 | 4 | 16 | 4 |

*Enterococcus faecium* CCUG37832: multiresistant, vanA-positive clinical isolate.
Mic (μg/ml): Ampicillin(20), Chlortetracycline (>10), erythromycin (>20), Lincomycin (>10), Vancomycin (>20), Apramycin (>20), Bacitracin (>8), Cycloserine (>8), Spectinomycin (>8), Sensitive: Gramicidin (0.01)

Example 6: Determination of In Vitro Cytotoxicity of MBL-AB01 and Xantolipin for IMR90 Fibroblast Cells The cytotoxicity of MBL-AB01 and Xantholipin was evaluated in in vitro assays with IMR90 Human Lung Fibroblast (ATCC CCL-186) cells. MBL-AB01 was isolated as described in example 5 above. Xantolipin was obtained from Shaghai Jiao Tong University, China. A stock solution of Xantolipin was established in methanol, and the concentration of the Xantolipin stock solution was correlated to MBL-AB01 on basis of UV/vis absorption by assuming that the compounds have similar extinction coefficients at 395 nm.

IMR90 cells were grown in DMEM—low glucose (Sigma) supplemented with 2 mM L-Glutamine, 1% MEM NEAA (Sigma), 1 mM Sodium Pyruvate, 10 mM HEPES and 100 U/mL Pen-Strep. The cells were subcultured twice or thrice a week at ratios between 1:2 and 1:8, depending on confluency. The day before exposure of the cells to the compounds, 30 μl of cell suspension with $1.2×10^5$ IMR90 cells per ml was seeded into 384-well plates (Corning Assay Plate, 3712) a using Tecan EVO robotic workstation with MCA384 pipetting unit using disposable tips (Tecan MCA 125 μl, 300 51 808). The microplates with cell suspension were shaken at 1600 rpm with 2.5 mm amplitude (Bioshake) for 20 seconds after seeding. The cell suspension was transferred to the microplates from a stirred reservoir (Reservoir flat base 300 mL 10723363) with sterile magnetic stirring bars (15×4.5 mm VWR 442-4522) at stirring at 350 rpm positioned on the on Tecan EVO. The microplates with the IMR90 cells were incubated at 37° C. with 5% CO2 atmosphere. At the day of the exposure of the cells serial dilutions of MBL-AB01 and Xantholipin were made in DMSO. The serial dilutions with the compounds were further diluted in cell culture medium and transferred to the assay wells, giving a total DMSO concentration in the assay wells of 0.6%. After exposure, the assay plates with the IMR90 cells were further incubated at 37° C. with 5% CO2 atmosphere for 24 hours. The viability of the cells after incubation was measured using the Promega CellTiter-GLO 2.0 viability assay. EC50 values for MBL-AB01 and Xantolipin were estimated based on the viability of exposed cell relative to the viability of control wells added growth medium with similar DMSO concentration. The EC50 value of MBL-AB01 was estimated to 20 µg/ml and the EC50 value of Xantholipin was estimated to 1 µg/ml for IMR90 cells in this assay.

DEPOSIT AND EXPERT SOLUTIONS

The applicant request that a sample of the deposited microorganism deposited under the Budapest Treaty with DSMZ on date Apr. 7, 2016 under deposit number DSM 32287 may only be made available to an expert, until the date on which the patent is granted.

REFERENCES

Behal, V. 2000. Bioactive products from *Streptomyces*. Advances in Applied Microbiology, Vol 47. 47:113-156.

Bennett, J. W., and R. Bentley. 1989. Whats in a Name-Microbial Secondary Metabolism. *Adv Appl Microbiol.* 34:1-28.

Bentley, S. D., K. F. Chater, A. M. Cerdeno-Tarraga, G. L. Challis, N. R. Thomson, K. D. James, D. E. Harris, M. A. Quail, H. Kieser, D. Harper, A. Bateman, S. Brown, G. Chandra, C. W. Chen, M. Collins, A. Cronin, A. Fraser, A. Goble, J. Hidalgo, T. Hornsby, S. Howarth, C. H. Huang, T. Kieser, L. Larke, L. Murphy, K. Oliver, S. O'Neil, E. Rabbinowitsch, M. A. Rajandream, K. Rutherford, S. Rutter, K. Seeger, D. Saunders, S. Sharp, R. Squares, S. Squares, K. Taylor, T. Warren, A. Wietzorrek, J. Woodward, B. G. Barrell, J. Parkhill, and D. A. Hopwood. 2002. Complete genome sequence of the model actinomycete *Streptomyces coelicolor* A3(2). Nature 417:141-147.

Berge S M, Bighley L D, Monkhouse D C. Pharmaceutical salts. J Pharm Sci. 1977 January; 66(1):1-19.

Bode, H. B., B. Bethe, R. Hofs, and A. Zeeck. 2002. Big effects from small changes: possible ways to explore nature's chemical diversity. Chembiochem 3:619-627

Brautaset, Trygve; Borgos, Sven Even F.; Sletta, Håvard; Ellingsen, Trond Erling; Zotchev, Sergey. (2003) Site-specific mutagenesis and domain substitutions in the loading module of the nystatin polyketide synthase, and their effects on nystatin synthesis in *Streptomyces noursei*. Journal of Biological Chemistry. vol. 278.

Cragg, G. M., P. G. Grothaus, and D. J. Newman. 2009. Impact of natural products on developing new anti-cancer agents. Chem. Rev. 109:3012-3043.

Fenical, W., and P. R. Jensen. 2006. Developing a new resource for drug discovery: marine actinomycete bacteria. Nat. Chem. Biol. 2:666-673.

Fischbach, M. A., and C. T. Walsh. 2006. Assembly-line enzymology for polyketide and nonribosomal peptide antibiotics: logic, machinery, and mechanisms. Chem. Rev. 106:3468-3496.

Engelhardt, K., K. F. Degnes, M. Kemmler, H. Bredholt, E. Fjaervik, G. Klinkenberg, H. Sletta, T. E. Ellingsen, and S. B. Zotchev. 2010. Production of a New Thiopeptide Antibiotic, TP-1161, by a Marine Nocardiopsis Species. *Appl Environ Microb.* 76:4969-4976.

Illing, G. T., I. D. Normansell, and J. F. Peberdy. 1989. Protoplast isolation and regeneration in *Streptomyces clavuligerus*. J. Gen. Microbiol. 135:2289-2297.

Manivasagan P, Venkatesan J, Sivakumar K, Kim S K Pharmaceutically active secondary metabolites of marine actinobacteria. Microbiol Res. 2014 April; 169(4):262-78. doi: 10.1016/j.micres.2013.07.014.

Magarvey, N. A., J. M. Keller, V. Bernan, M. Dworkin, and D. H. Sherman. 2004. Isolation and characterization of novel marine-derived actinomycete taxa rich in bioactive metabolites. Appl. Environ. Microbiol. 70:7520-7529.

Mincer, T. J., P. R. Jensen, C. A. Kauffman, and W. Fenical. 2002. Widespread and persistent populations of a major new marine actinomycete taxon in ocean sediments. Appl. Environ. Microbiol. 68:5005-5011.

ela'ez, F. 2006. The historical delivery of antibiotics from microbial natural products—can history repeat? Biochem. Pharmacol. 71:981-990.

Newman, D. J., and G. M. Cragg. 2007. Natural products as sources of new drugs over the last 25 years. J. Nat. Prod. 70:461-477.

Peak K K, Duncan K E, Luna V A, King D S, McCarthy P J, Cannons A C. Bacillus Strains Most Closely Related to Bacillus nealsonii Are Not Effectively Circumscribed within the Taxonomic Species Definition. Int J Microbiol. 2011; 2011:673136. doi: 10.1155/2011/673136. Epub 2011 Oct. 20

Riedlinger, J., A. Reicke, H. Zahner, B. Krismer, A. T. Bull, L. A. Maldonado, A. C. Ward, M. Goodfellow, B. Bister, D. Bischoff, R. D. Sussmuth, and H. P. Fiedler. 2004. Abyssomicins, inhibitors of the para-aminobenzoic acid pathway produced by the marine *Verrucosispora* strain AB-18-032. J. Antibiot. (Tokyo) 57:271-279.

Sekurova, O, Sletta H, T. E. E., Valla S, Zotchev S. 1999. Molecular cloning and analysis of a pleiotropic regulatory gene locus from the nystatin producer *Streptomyces noursei* ATCC11455. *FEMS Microbiology Letters.* 177, 297-304.

Thompson, C. J., J. M. Ward, and D. A. Hopwood. 1980. DNA cloning in *Streptomyces*: resistance genes from antibiotic-producing species. *Nature.* 286:525-527.

Wendt-Pienkowski, E., Y. Huang, J. Zhang, B. Li, H. Jiang, H. Kwon, C. R. Hutchinson, and B. Shen. 2005. Cloning, sequencing, analysis, and heterologous expression of the fredericamycin biosynthetic gene cluster from *Streptomyces griseus*. J. Am. Chem. Soc. 127:16442-16452.

Zotchev, Sergey. (2012) Marine actinomycetes as an emerging resource for the drug development pipelines. Journal of Biotechnology. vol. 158 (4).

The invention claimed is:

1. A compound, having the structure according to formula II and salts and solvates thereof,
wherein $R_1$ is a halogen atom selected from chlorine, bromine and iodine; $R_2$ and $R_3$ are —O-CH$_3$; $R_4$ is —COOH, -C(O)OR$_5$ or —C(O)NR$_5$R$_6$, wherein $R_5$ and $R_6$ are independently a hydrogen, a $C_1$-$C_4$-alkyl group, a $C_2$-$C_4$-alkenyl group, a $C_2$-$C_4$ alkenyl group, or a phenyl group.

2. A method for producing the compound according to claim 1, comprising
 a) cultivating a bacterium selected from the group consisting of:
  i) a bacterial isolate deposited under the Budapest Treaty with DSMZ on date Apr. 7, 2016 under deposit number DSM 32287; and
  ii) a bacteria which is closely related to the bacterial isolate of i;
 in a suitable culture medium comprising sea water; and
 b) extracting the compound from the culture.

3. The method of claim 2, wherein the bacterium comprises in its genome a 16S rRNA which by reverse transcription and second-strand synthesis provides a sequence which is at least 80% identical to the sequence of SEQ ID NO 1.

4. The method of claim 2, wherein step b) comprises centrifugation of the cultivated bacteria obtaining a cell pellet, from which the compound is extracted.

5. The method of claim 4, wherein the compound is extracted from the cell pellet using dimethyl sulfoxide (DMSO).

6. The method of claim 2, wherein the culture medium is PM6.

7. A pharmaceutical composition comprising the compound of claim 1, and a pharmaceutically acceptable carriers or excipients.

8. A method for treating a bacterial infection in a subject, comprising administering the compound according to claim 1 to the subject.

9. The method according to claim 8, wherein the bacterial infection is caused by a multidrug resistant bacterium.

10. The method according to claim 9, wherein the bacterial infection is caused by a Gram-positive or Gram-negative bacterium.

11. A method for killing or inhibiting the growth of a bacterium, comprising contacting the compound of claim 1 with the bacteria to be killed or inhibited.

12. A method for treating a bacterial infection in a subject, comprising administering the composition according to claim 7 to the subject.

13. A method for killing or inhibiting the growth of a bacterium, comprising contacting the composition of claim 7 with the bacteria to be killed or inhibited.

14. The method of claim 6, wherein the medium comprises artificial sea water.

15. The compound of claim 1 having Formula (III)

and salts and solvates thereof.

16. A pharmaceutical composition comprising the compound of claim 15, and a pharmaceutically acceptable carrier or excipient.

17. A method for treating a bacterial infection in a subject, comprising administering the compound according to claim 15 to the subject.

18. A method for treating a bacterial infection in a subject, comprising administering the composition according to claim 16 to the subject.

19. A method for killing or inhibiting the growth of a bacterium, comprising contacting the composition of claim 16 with the bacteria to be killed or inhibited.

* * * * *

SEQUENCE LISTING

<160> NUMBER OF SEQ ID NOS: 1

<210> SEQ ID NO 1
<211> LENGTH: 1458
<212> TYPE: DNA
<213> ORGANISM: Actinoalloteichus sp.

<400> SEQUENCE: 1

```
ggctcaggac gaacgctgcg gcgtgcttaa cacatgcaag tcgagcggta aggcccttcg      60
gggtacacga gcggcgaacg ggtgagtaac acgtgggtaa cctgccctgc actttggaat     120
```

```
aacctcggga aaccggggct aataccggat atgacatgtc atcgcatggt ggtgtgtgga    180
aagttccggc ggtgtgggat gggcccgcgg cctatcagct tgttggtggg gtgatggcct    240
accaaggcga cgacgggtag ccggcctgag agggcgaccg gccacactgg gactgagaca    300
cggcccagac tcctacggga ggcagcagtg gggaatattg cgcaatgggc gaaagcctga    360
cgcagcgacg ccgcgtgagg gatgactgcc ttcgggttgt aaacctcttt cagcgccgaa    420
gaagcgaaag tgacggtagg cgcagaagaa gcaccggcta actacgtgcc agcagccgcg    480
gtaatacgta gggtgcgagc gttgtccgga attattgggc gtaaagagct cgtaggcggt    540
ttgtcgcgtc ggctgtgaaa acctgggggct taacccggg cgtgcagtcg atacgggcag    600
acttgagttc ggcaggggag actggaattc ctggtgtagc ggtgaaatgc gcagatatca    660
ggaggaacac cggtggcgaa ggcgggtctc tgggccgata ctgacgctga ggagcgaaag    720
cgtggggagc gaacaggatt agataccctg tagtccacgc cgtaaacggt gggcgctagg    780 tgtggggat ttccacgtcc tccgtgccgt agctaacgca ttaagcgccc cgcctgggga    840
gtacggccgc aaggctaaaa ctcaaagaa ttgacgggg cccgcacgag cggcggagca    900
tgtggattaa ttcgatgcaa cgcgaagaac cttacctggg tttgacatgc accggacagc    960
ctcagagatg gggtttccgc aaggtcggtg tacaggtggt gcatggctgt cgtcagctcg   1020
tgtcgtgaga tgttgggtta agtcccgcaa cgagcgcaac ccttattcca tgttgccagc   1080
acgtaatggt ggggactcat gggagactgc cggggtcaac tcgaggaag gtggggacga   1140 cgtcaagtca tcatgcccct tatgtccagg gcttcacaca tgctacaatg gccggtacaa   1200
agggctgcta agccgtgagg tggagcgaat cccagaaagc cggtctcagt tcggatcggg   1260
gtctgcaact cgacccgtg aagtcggagt cgctagtaat cgcagatcag caacgctgcg   1320
gtgaatacgt tcccgggcct tgtacacacc gcccgtcacg tcacgaaagt cggtaacacc   1380
cgaagcccat ggcccaaccc gtgaggggg gagtggtcga aggtgggact ggcgattggg   1440
acgaagtcgt aacaaggt                                                  1458
```

UNITED STATES PATENT AND TRADEMARK OFFICE
CERTIFICATE OF CORRECTION

PATENT NO. : 10,494,375 B2
APPLICATION NO. : 16/095143
DATED : December 3, 2019
INVENTOR(S) : Havard Sletta et al.

Page 1 of 1

It is certified that error appears in the above-identified patent and that said Letters Patent is hereby corrected as shown below:

In the Specification

Column 4
Line 59, please delete "-$C(O)OR_1$ and –$C(O)NR_1R_2$, and $R_1$ and $R_2$" and substitute therefor
-- -$C(O)OR_5$ and –$C(O)NR_5R_6$, and $R_5$ and $R_6$--.

Signed and Sealed this
Second Day of June, 2020

Andrei Iancu
*Director of the United States Patent and Trademark Office*